United States Patent [19]

Nanba et al.

[11] Patent Number: 5,565,344
[45] Date of Patent: Oct. 15, 1996

[54] PROCESS FOR PRODUCTION OF D-α-AMINO ACIDS

[75] Inventors: Hirokazu Nanba, Takasago; Yukio Yamada, Kakogawa; Masayuki Takano; Yasuhiro Ikenaka, both of Akashi; Satomi Takahashi; Kazuyoshi Yajima, both of Kobe, all of Japan

[73] Assignee: Kanegafuchi Kagaku Kogyo Kabushiki Kaisha, Osaka, Japan

[21] Appl. No.: 917,111

[22] PCT Filed: Dec. 6, 1991

[86] PCT No.: PCT/JP91/01696

§ 371 Date: Aug. 7, 1992

§ 102(e) Date: Aug. 7, 1992

[87] PCT Pub. No.: WO92/10579

PCT Pub. Date: Jun. 25, 1992

[30] Foreign Application Priority Data

Dec. 7, 1990 [JP] Japan ..................... 2-400848
Dec. 27, 1990 [JP] Japan ..................... 2-407922
Apr. 11, 1991 [JP] Japan ..................... 3-078840

[51] Int. Cl.$^6$ ............... C12P 13/04; C12N 9/14; C12N 1/12; C07H 19/00
[52] U.S. Cl. ............... 435/106; 435/43; 435/69.1; 435/71.2; 435/176; 435/195; 435/227; 435/228; 435/252.3; 435/320.1; 536/22.1; 536/23.1; 536/23.2; 536/23.7
[58] Field of Search ............... 435/43, 69.1, 71.2, 435/106, 176, 195, 227, 228, 252.3, 320.1; 536/22.1, 23.1, 23.2, 23.7

[56] References Cited

FOREIGN PATENT DOCUMENTS

| | | |
|---|---|---|
| 0136359 | 4/1985 | European Pat. Off. . |
| 0261836 | 3/1988 | European Pat. Off. . |
| 55-88697 | 7/1980 | Japan . |
| 57-18793 | 4/1982 | Japan . |
| 63-24894 | 2/1988 | Japan . |
| 1534426 | 12/1978 | United Kingdom . |
| 2022581 | 12/1979 | United Kingdom . |

OTHER PUBLICATIONS

Oliveri et al. "Microbial transformation of racemic hydantorn. . ." 1981 *Biotech & Bioeng.* 23 pp. 2173–2183.
Glover "Principles of cloning DNA" *Gene Cloning* 1984 pp. 1–20.
Patent Abstracts of Japan, vol. 12, No. 230 (C–508)(3077), Jun. 29, 1988.

*Primary Examiner*—Robert A. Wax
*Assistant Examiner*—Hyosuk Kim
*Attorney, Agent, or Firm*—Foley & Lardner

[57] ABSTRACT

The present invention is directed to a gene which is related to a D-N-carbamoyl-α-amino acid amidohydrolase which is an enzyme capable of converting D-N-carbamoyl-α-amino acids into D-α-amino acids; a recombinant plasmid in which a DNA fragment containing the gene is incorporated into a vector; a microorganism belonging to the genus Escherichia, Pseudomonas, Flavobacterium, Bacillus, Serratia, Corynebacterium, or Brevibacterium, which is transformed by incorporating the recombinant plasmid thereinto; a process for the production of D-N-carbamoyl-α-amino acid amidohydrolases, comprising the steps of cultivating the transformed microorganism and collecting the desired product therefrom; a D-N-carbamoyl-α-amino acid amidohydrolase obtained by the method; and a process for the production of D-α-amino acids with the aid of an action of the enzyme.

The D-N-carbamoyl-α-amino acid amidohydrolase can be fixed on a support for immobilization and used as an immobilized enzyme.

13 Claims, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1785 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Agrobacterium radiobacter
        ( B ) STRAIN: KNK 712 (FERM BP- 1900)

( i x ) FEATURE:
        ( A ) NAME/KEY: CDS
        ( B ) LOCATION: 233..1141

( x i ) SEQUENCE DESCRIPTION: SEQ ID NO:1:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                              Thr
                                                              1
```

| CGT | CAG | ATG | ATA | CTT | GCA | GTG | GGA | CAA | CAA | GGT | CCG | ATC | GCG | CGC | GCG | 283 |
|---|---|---|---|---|---|---|---|---|---|---|---|---|---|---|---|---|
| Arg | Gln | Met | Ile | Leu | Ala | Val | Gly | Gln | Gln | Gly | Pro | Ile | Ala | Arg | Ala | |
| | | | 5 | | | | | 10 | | | | | 15 | | | |

| GAG | ACA | CGC | GAA | CAG | GTC | GTC | GTT | CGT | CTT | CTC | GAC | ATG | CTG | ACG | AAA | 331 |
|---|---|---|---|---|---|---|---|---|---|---|---|---|---|---|---|---|
| Glu | Thr | Arg | Glu | Gln | Val | Val | Val | Arg | Leu | Leu | Asp | Met | Leu | Thr | Lys | |
| | | 20 | | | | | 25 | | | | | 30 | | | | |

| GCC | GCG | AGC | CGG | GGC | GCG | AAT | TTC | ATT | GTC | TTC | CCC | GAA | CTC | GCG | CTT | 379 |
|---|---|---|---|---|---|---|---|---|---|---|---|---|---|---|---|---|
| Ala | Ala | Ser | Arg | Gly | Ala | Asn | Phe | Ile | Val | Phe | Pro | Glu | Leu | Ala | Leu | |
| 35 | | | | | 40 | | | | | 45 | | | | | | |

| ACG | ACC | TTC | TTC | CCG | CGC | TGG | CAT | TTC | ACC | GAC | GAG | GCC | GAG | CTC | GAT | 427 |
|---|---|---|---|---|---|---|---|---|---|---|---|---|---|---|---|---|
| Thr | Thr | Phe | Phe | Pro | Arg | Trp | His | Phe | Thr | Asp | Glu | Ala | Glu | Leu | Asp | |
| 50 | | | | | 55 | | | | 60 | | | | | | 65 | |

| AGC | TTC | TAT | GAG | ACC | GAA | ATG | CCC | GGC | CCG | GTG | GTC | CGT | CCA | CTC | TTT | 475 |
|---|---|---|---|---|---|---|---|---|---|---|---|---|---|---|---|---|
| Ser | Phe | Tyr | Glu | Thr | Glu | Met | Pro | Gly | Pro | Val | Val | Arg | Pro | Leu | Phe | |
| | | | | 70 | | | | | 75 | | | | | 80 | | |

| GAG | AAG | GCC | GCG | GAA | CTC | GGG | ATC | GGC | TTC | AAT | CTG | GGC | TAC | GCT | GAA | 523 |
|---|---|---|---|---|---|---|---|---|---|---|---|---|---|---|---|---|
| Glu | Lys | Ala | Ala | Glu | Leu | Gly | Ile | Gly | Phe | Asn | Leu | Gly | Tyr | Ala | Glu | |
| | | | 85 | | | | | 90 | | | | | 95 | | | |

| CTC | GTC | GTC | GAA | GGC | GGC | GTC | AAG | CGT | CGC | TTC | AAC | ACG | TCC | ATT | TTG | 571 |
|---|---|---|---|---|---|---|---|---|---|---|---|---|---|---|---|---|
| Leu | Val | Val | Glu | Gly | Gly | Val | Lys | Arg | Arg | Phe | Asn | Thr | Ser | Ile | Leu | |
| | | 100 | | | | | 105 | | | | | 110 | | | | |

| GTG | GAT | AAG | TCA | GGC | AAG | ATC | GTC | GGC | AAG | TAT | CGT | AAG | ATC | CAT | TTG | 619 |
|---|---|---|---|---|---|---|---|---|---|---|---|---|---|---|---|---|
| Val | Asp | Lys | Ser | Gly | Lys | Ile | Val | Gly | Lys | Tyr | Arg | Lys | Ile | His | Leu | |
| | 115 | | | | | 120 | | | | | 125 | | | | | |

| CCG | GGT | CAC | AAG | GAG | TAC | GAG | GCC | TAC | CGG | CCG | TTC | CAG | CAT | CTT | GAA | 667 |
|---|---|---|---|---|---|---|---|---|---|---|---|---|---|---|---|---|
| Pro | Gly | His | Lys | Glu | Tyr | Glu | Ala | Tyr | Arg | Pro | Phe | Gln | His | Leu | Glu | |
| 130 | | | | | 135 | | | | | 140 | | | | | 145 | |

| AAG | CGT | TAT | TTC | GAG | CCG | GGC | GAT | CTC | GGC | TTC | CCG | GTC | TAT | GAC | GTC | 715 |
|---|---|---|---|---|---|---|---|---|---|---|---|---|---|---|---|---|
| Lys | Arg | Tyr | Phe | Glu | Pro | Gly | Asp | Leu | Gly | Phe | Pro | Val | Tyr | Asp | Val | |
| | | | | 150 | | | | | 155 | | | | | 160 | | |

| GAC | GCC | GCG | AAA | ATG | GGG | ATG | TTC | ATC | TGC | AAC | GAT | CGC | CGC | TGG | CCT | 763 |
|---|---|---|---|---|---|---|---|---|---|---|---|---|---|---|---|---|
| Asp | Ala | Ala | Lys | Met | Gly | Met | Phe | Ile | Cys | Asn | Asp | Arg | Arg | Trp | Pro | |
| | | | 165 | | | | | 170 | | | | | 175 | | | |

| GAA | GCC | TGG | CGG | GTG | ATG | GGC | CTC | AGG | GGC | GCC | GAG | ATC | ATC | TGC | GGC | 811 |
|---|---|---|---|---|---|---|---|---|---|---|---|---|---|---|---|---|
| Glu | Ala | Trp | Arg | Val | Met | Gly | Leu | Arg | Gly | Ala | Glu | Ile | Ile | Cys | Gly | |
| | | 180 | | | | | 185 | | | | | 190 | | | | |

| GGC | TAC | AAC | ACG | CCG | ACC | CAC | AAT | CCC | CCT | GTT | CCC | CAG | CAC | GAC | CAC | 859 |
|---|---|---|---|---|---|---|---|---|---|---|---|---|---|---|---|---|
| Gly | Tyr | Asn | Thr | Pro | Thr | His | Asn | Pro | Pro | Val | Pro | Gln | His | Asp | His | |
| | 195 | | | | | 200 | | | | | 205 | | | | | |

| CTG | ACG | TCC | TTC | CAC | CAT | CTC | CTA | TCG | ATG | CAG | GCC | GGG | TCT | TAT | CAG | 907 |
|---|---|---|---|---|---|---|---|---|---|---|---|---|---|---|---|---|
| Leu | Thr | Ser | Phe | His | His | Leu | Leu | Ser | Met | Gln | Ala | Gly | Ser | Tyr | Gln | |
| 210 | | | | | 215 | | | | | 220 | | | | | 225 | |

| AAC | GGG | GCC | TGG | TCC | GCG | GCC | GCG | GGC | AAG | GTG | GGC | ATG | GAG | GAG | AAC | 955 |
|---|---|---|---|---|---|---|---|---|---|---|---|---|---|---|---|---|
| Asn | Gly | Ala | Trp | Ser | Ala | Ala | Ala | Gly | Lys | Val | Gly | Met | Glu | Glu | Asn | |
| | | | | 230 | | | | | 235 | | | | | 240 | | |

| TGC | ATG | CTG | CTC | GGC | CAC | TCC | TGC | ATC | GTG | GCG | CCG | ACC | GGG | GAA | ATC | 1003 |
|---|---|---|---|---|---|---|---|---|---|---|---|---|---|---|---|---|
| Cys | Met | Leu | Leu | Gly | His | Ser | Cys | Ile | Val | Ala | Pro | Thr | Gly | Glu | Ile | |
| | | | 245 | | | | | 250 | | | | | 255 | | | |

| GTC | GCT | CTC | ACT | ACG | ACG | CTG | GAA | GAC | GAG | GTG | ATC | ACC | GCC | GCC | GTC | 1051 |
|---|---|---|---|---|---|---|---|---|---|---|---|---|---|---|---|---|
| Val | Ala | Leu | Thr | Thr | Thr | Leu | Glu | Asp | Glu | Val | Ile | Thr | Ala | Ala | Val | |
| | | 260 | | | | | 265 | | | | | 270 | | | | |

| GAT | CTC | GAT | CGC | TGC | CGG | GAA | CTG | CGT | GAA | CAC | ATC | TTC | AAC | TTC | AAG | 1099 |
|---|---|---|---|---|---|---|---|---|---|---|---|---|---|---|---|---|

| Asp | Leu | Asp | Arg | Cys | Arg | Glu | Leu | Arg | Glu | His | Ile | Phe | Asn | Phe | Lys |
|  | 275 |  |  |  | 280 |  |  |  |  | 285 |  |  |  |  |  |

| CAG | CAT | CGT | CAG | CCC | CAG | CAC | TAT | GGT | CTG | ATC | GCG | GAA | CTC |  | 1141 |
|---|---|---|---|---|---|---|---|---|---|---|---|---|---|---|---|
| Gln | His | Arg | Gln | Pro | Gln | His | Tyr | Gly | Leu | Ile | Ala | Glu | Leu |  |  |
| 290 |  |  |  |  | 295 |  |  |  |  | 300 |  |  |  |  |  |

| TGAGGTTGCC | GAAAAGCATG | TGTGTCGTTG | TTCTCGGCGC | CTGGGTCACA | TCCAGGCGCG | 1201 |
| CCAGGGTGAC | GCTGGTGGAA | TAGTACCACG | ACCGCTTCAG | GGCGATCCGC | AAGGAGATGC | 1261 |
| GGGTCGCCGG | AGCGGCAAAG | CCCGACATTC | GTTTCGCACC | GACGGCCGTC | GTGAACTCGA | 1321 |
| CAGTCCGCGA | GAAGGGCGTA | TTGCGCGGCC | TGGACCTGTA | CGTGGAACTG | TAGCCCATAT | 1381 |
| ATAGATTTCC | AAAGAGTTTC | GGCGAGGCGC | GGCGCGCCTA | GCCCATGTG | AGCGAGAACC | 1441 |
| GTGCCCAGAT | CAAAGAATGA | GACCGACGCG | CCGGCCGCGG | CAAAGGATGA | TCCTCAGGGT | 1501 |
| CGGATCTATC | GCTCCGCCCT | GAAGCAGGAG | GGCGCACGCT | GGCTGCTGAC | GGCGGAGGAA | 1561 |
| GGGTTGCTGG | CAAAGCCCAA | GCCGCCCGGC | CTTGTTCCGG | CACTTGAGAA | TGCGATCGCC | 1621 |
| ATCGTCGATT | ACATCAACGG | TACACCGCCC | CATATCGCGT | CCCTGGCGGA | GCTTTCAACG | 1681 |
| ACGCTCGGGA | TATCCAAGAG | CCACTGTCAC | TCCATCCTCA | AGACGCTGAC | GCATTTCGGC | 1741 |
| TGGCTGAAAT | TCGACAATCG | CTCAAAGAGC | TACGAGCTGA | ATTC |  | 1785 |

( 2 ) INFORMATION FOR SEQ ID NO:2:

( i ) SEQUENCE CHARACTERISTICS:
        ( A ) LENGTH: 303 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Thr | Arg | Gln | Met | Ile | Leu | Ala | Val | Gly | Gln | Gln | Gly | Pro | Ile | Ala | Arg |
| 1 |  |  |  | 5 |  |  |  |  | 10 |  |  |  |  | 15 |  |

| Ala | Glu | Thr | Arg | Glu | Gln | Val | Val | Arg | Leu | Leu | Asp | Met | Leu | Thr |
|  |  |  | 20 |  |  |  | 25 |  |  |  | 30 |  |  |  |

| Lys | Ala | Ala | Ser | Arg | Gly | Ala | Asn | Phe | Ile | Val | Phe | Pro | Glu | Leu | Ala |
|  |  | 35 |  |  |  |  | 40 |  |  |  | 45 |  |  |  |  |

| Leu | Thr | Thr | Phe | Phe | Pro | Arg | Trp | His | Phe | Thr | Asp | Glu | Ala | Glu | Leu |
|  | 50 |  |  |  |  | 55 |  |  |  |  | 60 |  |  |  |  |

| Asp | Ser | Phe | Tyr | Glu | Thr | Glu | Met | Pro | Gly | Pro | Val | Val | Arg | Pro | Leu |
| 65 |  |  |  |  | 70 |  |  |  |  | 75 |  |  |  |  | 80 |

| Phe | Glu | Lys | Ala | Ala | Glu | Leu | Gly | Ile | Gly | Phe | Asn | Leu | Gly | Tyr | Ala |
|  |  |  |  | 85 |  |  |  |  | 90 |  |  |  |  | 95 |  |

| Glu | Leu | Val | Val | Glu | Gly | Gly | Val | Lys | Arg | Arg | Phe | Asn | Thr | Ser | Ile |
|  |  |  | 100 |  |  |  |  | 105 |  |  |  |  | 110 |  |  |

| Leu | Val | Asp | Lys | Ser | Gly | Lys | Ile | Val | Gly | Lys | Tyr | Arg | Lys | Ile | His |
|  |  | 115 |  |  |  |  | 120 |  |  |  |  | 125 |  |  |  |

| Leu | Pro | Gly | His | Lys | Glu | Tyr | Glu | Ala | Tyr | Arg | Pro | Phe | Gln | His | Leu |
|  | 130 |  |  |  |  | 135 |  |  |  |  | 140 |  |  |  |  |

| Glu | Lys | Arg | Tyr | Phe | Glu | Pro | Gly | Asp | Leu | Gly | Phe | Pro | Val | Tyr | Asp |
| 145 |  |  |  |  | 150 |  |  |  |  | 155 |  |  |  |  | 160 |

| Val | Asp | Ala | Ala | Lys | Met | Gly | Met | Phe | Ile | Cys | Asn | Asp | Arg | Arg | Trp |
|  |  |  |  | 165 |  |  |  |  | 170 |  |  |  |  | 175 |  |

| Pro | Glu | Ala | Trp | Arg | Val | Met | Gly | Leu | Arg | Gly | Ala | Glu | Ile | Ile | Cys |
|  |  |  | 180 |  |  |  |  | 185 |  |  |  |  | 190 |  |  |

| Gly | Gly | Tyr | Asn | Thr | Pro | Thr | His | Asn | Pro | Pro | Val | Pro | Gln | His | Asp |
|  |  | 195 |  |  |  |  | 200 |  |  |  |  | 205 |  |  |  |

```
His  Leu  Thr  Ser  Phe  His  His  Leu  Leu  Ser  Met  Gln  Ala  Gly  Ser  Tyr
     210                     215                     220

Gln  Asn  Gly  Ala  Trp  Ser  Ala  Ala  Ala  Gly  Lys  Val  Gly  Met  Glu  Glu
225                      230                     235                          240

Asn  Cys  Met  Leu  Leu  Gly  His  Ser  Cys  Ile  Val  Ala  Pro  Thr  Gly  Glu
               245                      250                     255

Ile  Val  Ala  Leu  Thr  Thr  Thr  Leu  Glu  Asp  Glu  Val  Ile  Thr  Ala  Ala
               260                     265                     270

Val  Asp  Leu  Asp  Arg  Cys  Arg  Glu  Leu  Arg  Glu  His  Ile  Phe  Asn  Phe
          275                     280                     285

Lys  Gln  His  Arg  Gln  Pro  Gln  His  Tyr  Gly  Leu  Ile  Ala  Glu  Leu
     290                     295                     300
```

( 2 ) INFORMATION FOR SEQ ID NO:3:

( i ) SEQUENCE CHARACTERISTICS:
        ( A ) LENGTH: 303 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Agrobacterium radiobacter
        ( B ) STRAIN: KNK 712 (FERM BP- 1900)

( x i ) SEQUENCE DESCRIPTION: SEQ ID NO:3:

```
Thr  Arg  Gln  Met  Ile  Leu  Ala  Val  Gly  Gln  Gln  Gly  Pro  Ile  Ala  Arg
1                   5                    10                      15

Ala  Glu  Thr  Arg  Glu  Gln  Val  Val  Arg  Leu  Leu  Asp  Met  Leu  Thr
               20                      25                      30

Lys  Ala  Ala  Ser  Arg  Gly  Ala  Asn  Phe  Ile  Val  Phe  Pro  Glu  Leu  Ala
          35                      40                      45

Leu  Thr  Thr  Phe  Phe  Pro  Arg  Trp  His  Phe  Thr  Asp  Glu  Ala  Glu  Leu
     50                      55                      60

Asp  Ser  Phe  Tyr  Glu  Thr  Glu  Met  Pro  Gly  Pro  Val  Val  Arg  Pro  Leu
65                       70                      75                           80

Phe  Glu  Lys  Ala  Ala  Glu  Leu  Gly  Ile  Gly  Phe  Asn  Leu  Gly  Tyr  Ala
                    85                      90                      95

Glu  Leu  Val  Val  Glu  Gly  Gly  Val  Lys  Arg  Arg  Phe  Asn  Thr  Ser  Ile
                    100                     105                     110

Leu  Val  Asp  Lys  Ser  Gly  Lys  Ile  Val  Gly  Lys  Tyr  Arg  Lys  Ile  His
               115                     120                     125

Leu  Pro  Gly  His  Lys  Glu  Tyr  Glu  Ala  Tyr  Arg  Pro  Phe  Gln  His  Leu
     130                     135                     140

Glu  Lys  Arg  Tyr  Phe  Glu  Pro  Gly  Asp  Leu  Gly  Phe  Pro  Val  Tyr  Asp
145                     150                     155                          160

Val  Asp  Ala  Ala  Lys  Met  Gly  Met  Phe  Ile  Cys  Asn  Asp  Arg  Arg  Trp
                    165                     170                     175

Pro  Glu  Ala  Trp  Arg  Val  Met  Gly  Leu  Arg  Gly  Ala  Glu  Ile  Ile  Cys
               180                     185                     190

Gly  Gly  Tyr  Asn  Thr  Pro  Thr  His  Asn  Pro  Pro  Val  Pro  Gln  His  Asp
               195                     200                     205

His  Leu  Thr  Ser  Phe  His  His  Leu  Leu  Ser  Met  Gln  Ala  Gly  Ser  Tyr
     210                     215                     220

Gln  Asn  Gly  Ala  Trp  Ser  Ala  Ala  Ala  Gly  Lys  Val  Gly  Met  Glu  Glu
225                     230                     235                          240
```

```
         Asn  Cys  Met  Leu  Leu  Gly  His  Ser  Cys  Ile  Val  Ala  Pro  Thr  Gly  Glu
                        245                      250                      255

Ile  Val  Ala  Leu  Thr  Thr  Thr  Leu  Glu  Asp  Glu  Val  Ile  Thr  Ala  Ala
                        260                      265                      270

Val  Asp  Leu  Asp  Arg  Cys  Arg  Glu  Leu  Arg  Glu  His  Ile  Phe  Asn  Phe
                        275                      280                      285

Lys  Gln  His  Arg  Gln  Pro  Gln  His  Tyr  Gly  Leu  Ile  Ala  Glu  Leu
                        290                      295                      300
```

( 2 ) INFORMATION FOR SEQ ID NO:4:

( i ) SEQUENCE CHARACTERISTICS:
        ( A ) LENGTH: 1820 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Pseudomonas
        ( B ) STRAIN: KNK 003A (FERM BP- 3181)

( i x ) FEATURE:
        ( A ) NAME/KEY: CDS
        ( B ) LOCATION: 701..1633

( x i ) SEQUENCE DESCRIPTION: SEQ ID NO:4:

```
GCATGCGCGG  GGAACTGAAG  AACTTGCAAG  ACGAACTCGG  CATTACCTTC  GTGCATGTAA      60

CCCATACCCA  GCCTGAGGCG  ATCGCGCTCG  CCGACATGGT  GGTTGTGATG  GATACGGGCC     120

GCATAGAGCA  GGCAGCGAGC  GCCAACGAAA  TCTACAACCG  GCCCGCGACG  CCCTATGTGG     180

CGCGCTTCAT  GGGCGGCCAA  AACGTGTTGA  CGGGGAGGGT  GGAGAGCATC  TCGCCCACCG     240

GCATGGTGCT  GAAAAGCGAA  AAGGGCGAGA  TCTTCAATGC  GCCTCTTACG  GGTGCTGCGC     300

CGAAGCTGGG  CGAACCCGTA  TCGATATCCA  TGCGCCGCGA  CCGCATCAGC  ATCAGCAAGC     360

CGCAAAACGG  CAAGGGCGCG  CAGCAGGCTG  ACGCGGTAAC  GGGTGTGGTC  GATTCCACGG     420

AATACCAGGG  CAGCTTCGTG  AAGGTCAGCA  TAGTGCTCGA  CGGTGGCGAG  ACCTTCGTCG     480

CAAACATGCC  CGACCATGAA  TTTTTCGCGG  AACCGGTGGA  TCACGGCGTC  CCGGTGGTCG     540

CCCGCTGGAA  ACCGGAGCAT  GTGCATGTCC  TGTCCAAGTC  TGACCGGGGC  GCCGACCACA     600

CCGAAATCTA  CCGCTTCCCT  GCAGGCGAAA  ATACCGTTTC  AATGGGCAAG  GGGCGGCAAA     660

CGGGGTTGAG  ACGACCCGGT  TTATCGAGGA  GGACGAGATG  ACA CGC ATC GTC AAT        715
                                                Thr Arg Ile Val Asn
                                                 1                5

GCA GCC GCC GCG CAG ATG GGG CCC ATC AGC CGG TCC GAA ACG CGC AAG            763
Ala Ala Ala Ala Gln Met Gly Pro Ile Ser Arg Ser Glu Thr Arg Lys
              10                  15                  20

GAT ACG GTC CGG CGC CTG ATC GCG CTC ATG CGC GAG GCG AAG GCC CGC            811
Asp Thr Val Arg Arg Leu Ile Ala Leu Met Arg Glu Ala Lys Ala Arg
             25                  30                  35

GGT TCC GAC CTT GTC GTC TTT ACC GAA CTC GCG CTC ACC ACC TTC TTT            859
Gly Ser Asp Leu Val Val Phe Thr Glu Leu Ala Leu Thr Thr Phe Phe
             40                  45                  50

CCC CGC TGG GTG ATC GAG GAC GAA GCT GAG CTC GAC AGC TTC TAC GAG            907
Pro Arg Trp Val Ile Glu Asp Glu Ala Glu Leu Asp Ser Phe Tyr Glu
     55                  60                  65

AAG GAG ATG CCA GGG CCC GAA ACC CAG CCG CTC TTC GAT GAG GCG AAG            955
Lys Glu Met Pro Gly Pro Glu Thr Gln Pro Leu Phe Asp Glu Ala Lys
 70                  75                  80                  85

CGC TTG GAG ATC GGC TTC TAT CTC GGT TAT GCC GAG CTG GCG GAG GAG           1003
```

| | | | | | | | | | | | | | | |
|---|---|---|---|---|---|---|---|---|---|---|---|---|---|---|
|Arg|Leu|Glu|Ile|Gly<br>90|Phe|Tyr|Leu|Gly|Tyr<br>95|Ala|Glu|Leu|Ala|Glu<br>100|Glu|

| | | | | | | | | | | | | | | | |
|---|---|---|---|---|---|---|---|---|---|---|---|---|---|---|---|
|GGC|GGC|AGG|AAG|CGG|CGC|TTC|AAC|ACC|TCT|ATC|CTT|GTG|GAC|CGC|AGC|
|Gly|Gly|Arg|Lys<br>105|Arg|Arg|Phe|Asn|Thr|Ser<br>110|Ile|Leu|Val|Asp|Arg<br>115|Ser|

1051

GGC CGG ATC GTC GGC AAG TAC CGC AAG GTG CAC CTG CCC GGG CAC AAA     1099
Gly Arg Ile Val Gly Lys Tyr Arg Lys Val His Leu Pro Gly His Lys
        120             125                 130

GAG CCG CAG CCC GGC AGG AAA CAC CAG CAT CTC GAG AAA CGC TAT TTC     1147
Glu Pro Gln Pro Gly Arg Lys His Gln His Leu Glu Lys Arg Tyr Phe
        135             140                 145

GAG CCC GGC GAT CTC GGC TTC GGT GTC TGG CGC GCC TTC GAC GGC GTA     1195
Glu Pro Gly Asp Leu Gly Phe Gly Val Trp Arg Ala Phe Asp Gly Val
150             155                 160                 165

ATG GGC ATG TGC ATT TGC AAC GAC CGC CGC TGG CCG GAG ACC TAC CGG     1243
Met Gly Met Cys Ile Cys Asn Asp Arg Arg Trp Pro Glu Thr Tyr Arg
                170             175                 180

GTC ATG GGC TTG CAG GGA GTG GAG ATG GTC ATG CTG GGC TAC AAC ACG     1291
Val Met Gly Leu Gln Gly Val Glu Met Val Met Leu Gly Tyr Asn Thr
            185             190                 195

CCG TAT GAC CAT ACC GGT CAC GAC GAC ATC GAT TCA CTC ACC CAG TTT     1339
Pro Tyr Asp His Thr Gly His Asp Asp Ile Asp Ser Leu Thr Gln Phe
        200             205                 210

CAC AAT CAT CTC TCC ATG CAG GCG GGC GCC TAC CAG AAT TCG ACC TGG     1387
His Asn His Leu Ser Met Gln Ala Gly Ala Tyr Gln Asn Ser Thr Trp
        215             220                 225

GTG ATC GGC ACC GCC AAA TGC GGC ACC GAG GAG GGC TCC AAA ATG GTG     1435
Val Ile Gly Thr Ala Lys Cys Gly Thr Glu Glu Gly Ser Lys Met Val
230             235                 240                 245

GGG CAG AGC GTG ATC GTT GCG CCC TCG GGC GAG ATC GTC GCT ATG GCC     1483
Gly Gln Ser Val Ile Val Ala Pro Ser Gly Glu Ile Val Ala Met Ala
            250             255                 260

TGC ACG ATC GAG GAC GAG ATC ATC ACC GCA CGC TGC GAT CTC GAC ATG     1531
Cys Thr Ile Glu Asp Glu Ile Ile Thr Ala Arg Cys Asp Leu Asp Met
            265             270                 275

GGC AAG CGC TAC CGC GAG ACC ATC TTC GAT TTC GCC CGC CAT CGC GAG     1579
Gly Lys Arg Tyr Arg Glu Thr Ile Phe Asp Phe Ala Arg His Arg Glu
        280             285                 290

CCC GAC GCC TAT CGC CTG ATC GTC GAA CGC AAA GGG GCT GTG CCG CCG     1627
Pro Asp Ala Tyr Arg Leu Ile Val Glu Arg Lys Gly Ala Val Pro Pro
        295             300                 305

CCG CAG TGATCGGAAC CTGAAAACGA AATATCCCGC CGGACGGTGG AAGGTGAAA       1683
Pro Gln
310

GGAGGAGTCT CCATGACAAC AGTTATCAAG GGTGGAACAT CGTCGCCGCC GATCGCAGCT   1743

ATGAAGCCGA TATCCTGATC GAAGGCGAAA AGATCGCCCA GATCGGCAGG GATCTGCAGG   1803

GCGACAAGAT TGTCGAC                                                  1820

( 2 ) INFORMATION FOR SEQ ID NO:5:

( i ) SEQUENCE CHARACTERISTICS:
        ( A ) LENGTH: 311 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

Thr Arg Ile Val Asn Ala Ala Ala Ala Gln Met Gly Pro Ile Ser Arg
 1               5                  10                  15

| Ser | Glu | Thr | Arg | Lys | Asp | Thr | Val | Arg | Arg | Leu | Ile | Ala | Leu | Met | Arg |
|---|---|---|---|---|---|---|---|---|---|---|---|---|---|---|---|
| | | | 20 | | | | 25 | | | | | 30 | | | |

Glu Ala Lys Ala Arg Gly Ser Asp Leu Val Val Phe Thr Glu Leu Ala
              35                    40                  45

Leu Thr Thr Phe Phe Pro Arg Trp Val Ile Glu Asp Glu Ala Glu Leu
        50                  55                  60

Asp Ser Phe Tyr Glu Lys Glu Met Pro Gly Pro Glu Thr Gln Pro Leu
65                  70                  75                      80

Phe Asp Glu Ala Lys Arg Leu Glu Ile Gly Phe Tyr Leu Gly Tyr Ala
                85                  90                      95

Glu Leu Ala Glu Glu Gly Gly Arg Lys Arg Arg Phe Asn Thr Ser Ile
            100                 105                 110

Leu Val Asp Arg Ser Gly Arg Ile Val Gly Lys Tyr Arg Lys Val His
        115                 120                 125

Leu Pro Gly His Lys Glu Pro Gln Pro Gly Arg Lys His Gln His Leu
    130                 135                 140

Glu Lys Arg Tyr Phe Glu Pro Gly Asp Leu Gly Phe Gly Val Trp Arg
145                 150                 155                 160

Ala Phe Asp Gly Val Met Gly Met Cys Ile Cys Asn Asp Arg Arg Trp
                165             170                 175

Pro Glu Thr Tyr Arg Val Met Gly Leu Gln Gly Val Glu Met Val Met
            180                 185                 190

Leu Gly Tyr Asn Thr Pro Tyr Asp His Thr Gly His Asp Ile Asp
        195                 200                 205

Ser Leu Thr Gln Phe His Asn His Leu Ser Met Gln Ala Gly Ala Tyr
    210                 215                 220

Gln Asn Ser Thr Trp Val Ile Gly Thr Ala Lys Cys Gly Thr Glu Glu
225                 230                 235                 240

Gly Ser Lys Met Val Gly Gln Ser Val Ile Val Ala Pro Ser Gly Glu
            245                 250                 255

Ile Val Ala Met Ala Cys Thr Ile Glu Asp Glu Ile Ile Thr Ala Arg
            260                 265                 270

Cys Asp Leu Asp Met Gly Lys Arg Tyr Arg Glu Thr Ile Phe Asp Phe
        275                 280                 285

Ala Arg His Arg Glu Pro Asp Ala Tyr Arg Leu Ile Val Glu Arg Lys
    290                 295                 300

Gly Ala Val Pro Pro Pro Gln
305                 310

( 2 ) INFORMATION FOR SEQ ID NO:6:

( i ) SEQUENCE CHARACTERISTICS:
        ( A ) LENGTH: 311 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Pseudomonas
        ( B ) STRAIN: KNK 003A (FERM BP- 3181)

( x i ) SEQUENCE DESCRIPTION: SEQ ID NO:6:

Thr Arg Ile Val Asn Ala Ala Ala Ala Gln Met Gly Pro Ile Ser Arg
1               5                   10                  15

Ser Glu Thr Arg Lys Asp Thr Val Arg Arg Leu Ile Ala Leu Met Arg
            20                  25                  30

| | | | | | | | | | | | | | | |
|---|---|---|---|---|---|---|---|---|---|---|---|---|---|---|
| Glu | Ala | Lys 35 | Ala | Arg | Gly | Ser | Asp 40 | Leu | Val | Val | Phe 45 | Thr | Leu | Ala |
| Leu | Thr 50 | Thr | Phe | Phe | Pro | Arg 55 | Trp | Val | Ile | Glu | Asp 60 | Glu | Ala | Glu | Leu |
| Asp 65 | Ser | Phe | Tyr | Glu | Lys 70 | Glu | Met | Pro | Gly | Pro 75 | Glu | Thr | Gln | Pro | Leu 80 |
| Phe | Asp | Glu | Ala | Lys 85 | Arg | Leu | Glu | Ile | Gly 90 | Phe | Tyr | Leu | Gly | Tyr 95 | Ala |
| Glu | Leu | Ala | Glu 100 | Glu | Gly | Gly | Arg | Lys 105 | Arg | Arg | Phe | Asn | Thr 110 | Ser | Ile |
| Leu | Val | Asp 115 | Arg | Ser | Gly | Arg | Ile 120 | Val | Gly | Lys | Tyr | Arg 125 | Lys | Val | His |
| Leu | Pro 130 | Gly | His | Lys | Glu | Pro 135 | Gln | Pro | Gly | Arg | Lys 140 | His | Gln | His | Leu |
| Glu 145 | Lys | Arg | Tyr | Phe | Glu 150 | Pro | Gly | Asp | Leu | Gly 155 | Phe | Gly | Val | Trp | Arg 160 |
| Ala | Phe | Asp | Gly | Val 165 | Met | Gly | Met | Cys | Ile 170 | Cys | Asn | Asp | Arg | Arg 175 | Trp |
| Pro | Glu | Thr | Tyr 180 | Arg | Val | Met | Gly | Leu 185 | Gln | Gly | Val | Glu | Met 190 | Val | Met |
| Leu | Gly | Tyr 195 | Asn | Thr | Pro | Tyr | Asp 200 | His | Thr | Gly | His | Asp 205 | Asp | Ile | Asp |
| Ser | Leu 210 | Thr | Gln | Phe | His | Asn 215 | His | Leu | Ser | Met | Gln 220 | Ala | Gly | Ala | Tyr |
| Gln 225 | Asn | Ser | Thr | Trp | Val 230 | Ile | Gly | Thr | Ala | Lys 235 | Cys | Gly | Thr | Glu | Glu 240 |
| Gly | Ser | Lys | Met | Val 245 | Gly | Gln | Ser | Val | Ile 250 | Val | Ala | Pro | Ser | Gly 255 | Glu |
| Ile | Val | Ala | Met 260 | Ala | Cys | Thr | Ile | Glu 265 | Asp | Glu | Ile | Ile | Thr 270 | Ala | Arg |
| Cys | Asp | Leu 275 | Asp | Met | Gly | Lys | Arg 280 | Tyr | Arg | Glu | Thr | Ile 285 | Phe | Asp | Phe |
| Ala | Arg 290 | His | Arg | Glu | Pro | Asp 295 | Ala | Tyr | Arg | Leu | Ile 300 | Val | Glu | Arg | Lys |
| Gly 305 | Ala | Val | Pro | Pro | Pro 310 | Gln | | | | | | | | | |

PROCESS FOR PRODUCTION OF D-α-AMINO ACIDS

TECHNICAL FIELD

The present invention relates to a process for the production of D-α-amino acids, and more particularly, to a process for the production of D-α-amino acids using a novel transformant having a gene which is related to an enzyme capable of converting D-N-carbamoyl-α-amino acids into the corresponding D-α-amino acids.

BACKGROUND ART

Optically-active D-α-amino acids are important compounds as intermediates of drugs, and particularly, D-phenylglycine, D-parahydroxyphenyl-glycine and other intermediates for the production of semisynthesized penicillin or cephalosporin antibiotics are industrially useful compounds. As a process for the production of such D-α-amino acids, there is a well-known process in which carbamoyl groups of the corresponding D-N-carbamoyl-α-amino acids are removed to give the desired D-α-amino acids. The removal of carbamoyl groups in this process is achieved by a chemical process (e.g., the specification of Japanese Patent Publication No. 58-4707) or by a process utilizing the enzymatic reaction of microorganisms (e.g., the specifications of Japanese Patent Publication Nos. 57-18793, 63-20520, and 1-48758).

PROBLEMS TO BE SOLVED BY THE INVENTION

In a chemical process employed for the removal of carbamoyl groups as described above, a great amount of mineral acid such as sulfuric acid is used, and therefore, there will occur serious environmental problems regarding to the disposal thereof and the like. On the other hand, a process utilizing the enzymatic reaction of microorganisms has several drawbacks that microorganisms hitherto known as a source of enzyme supply cannot produce a sufficient amount of enzymes and that expensive hydantoin or N-carbamoylamino acid compounds are required for the production of enzymes.

MEANS FOR SOLVING THE PROBLEMS

For the purpose of solving such problems, the objects of the present invention are to prepare microorganisms having high productivity of enzymes, as well as to produce D-α-amino acids with high efficiency by use of a source of enzyme supply thus obtained.

A similar technique is disclosed in Japanese Patent Laid-open Publication No. 63-24894. However, this technique relates to the production of L-α-amino acids, and there is no experimental example describing the production of D-α-amino acids.

The present invention provides a process for the production of D-α-amino acids, characterized in that D-N-carbamoyl-α-amino acids are converted into the corresponding D-α-amino acids in an aqueous medium with the aid of an action of an enzyme produced from a transformant which is obtained by transformation of host bacterial cells selected from the microorganisms belonging to the genera Escherichia, Pseudomonas, Flavobacterium, Bacillus, Serratia, Corynebacterium, and Brevibacterium, with a recombinant DNA comprising a vector DNA and a DNA fragment containing a gene which is related to that enzyme capable of converting D-N-carbamoyl-α-amino acids by removal of their carbamoyl groups into the corresponding D-α-amino acids, after which the D-α-amino acids produced are collected.

By the way, no example has hitherto been known that a recombinant DNA comprising a vector and a gene which is related to an enzyme capable of converting D-N-carbamoyl-α-amino acids by removal of their carbamoyl groups into the corresponding D-α-amino acids is incorporated into microorganisms to achieve the expression of the gene. Such a technique was not succeeded until the present invention has been completed.

The enzymes capable of converting D-N-carbamoyl-α-amino acids by removal of their carbamoyl groups into the corresponding D-α-amino acids are, in fact, not limited to those which specifically act on the D-isomers or those which act on either D- or L-isomers. In particular, enzymes having a strict stereoselectivity to D-N-carbamoyl-α-amino acids may be referred to as D-N-carbamoyl-α-amino acid amidohydrolases Examples of the DNA fragment containing a gene which can be used in the present invention are those which are derived from eucaryotes, prokaryotes, viruses, bacteriophages or plasmids, and which contain a gene related to a particular D-N-carbamoyl-α-amino acid amidohydrolase. As the gene derived from prokaryotes, preferred are those which are derived from bacteria belonging to the genus, for example, Pseudomonas, Agrobacterium, Aerobacter, Aeromonas, Brevibacterium, Bacillus, Flavobacterium, Serratia, Micrococcus, Arthrobacter, Alkaligenes, Achromobacter, Moraxella, or Paracoccus, and which are related to D-N-carbamoyl-α-amino-acid amidohydrolases. Specific examples of such strains are as follows: *Aerobacter cloacae* IAM 1221, *Bacillus macroides* ATCC 12905, *Bacillus alvei* IFO 3343, *Brevibacterium ammoniagenes* IFO 12071, *Flavobacterium flavescens* IFO 3086, *Sarcina lutea* IFO 1099, *Serratia marcescens* IFO 3054, *Micrococcus luteus* IFO 12708, *Aeromonas hydrophilia* IFO 3820, *Agrobacterium radiobacter* KNK 712 (FERM BP-1900), Pseudomonas-sp. KNK 003A (FERM BP-3181), Pseudomonas sp. KNK 505 (FERM BP-3182), Agrobacterium 1302 NRRL B11291, *Alkaligenes aquamarinus* AJ 11199, *Achromobacter liquefaciens* AJ 11198, *Moraxella nonliquefaciens* AJ 11221, *Paracoccus denitrificans* AJ 11222, *Arthrobacter fragilus* AJ 1123, and the like.

As the typical examples of the above bacteria, the micological characteristics of *Agrobacterium radiobacter* KNK 712 (FERM BP-1900), Pseudomonas sp. KNK 003A (FERM BP-3181), and Pseudomonas sp. KNK 505 (FERM BP-3182) are described below.

*Agrobacterium radiobatter* KNK 712 (FERM BP-1900)

(a) Morphology
   (1) Cell size and shape: 0.5–1.0×2.0–4.0 μm, rods
   (2) Cellular polymorphism: none
   (3) Motility and flagellar arrangement: active, subpolar
   (4) Sporulation: none
   (5) Gram-staining: negative
(b) Cultural characteristics on various media
   (1) Meat extract agar plate culture: satisfactory growth, round, ridgy, smooth margin, smooth wet surface, white to cream-colored, glossy, opaque, liquid form
   (2) Meat extract agar slant culture: excellent growth, even growth on the inoculation line, thick ridge, smooth wet surface, smooth margin, white to cream-colored, glossy, opaque, no change in the medium (3) Meat extract gelatin stab culture: feeble growth, growth along the stab line, growth around the stab line, no gelatin liquefaction, white to cream-colored, no change in transparency, no change in the medium (4) Meat extract liquid culture: medium growth, uneven turbidity, flock formation, no surface growth (5) Litmus milk: weak acid (c) Physiological Characteristics (1) Nitrate reduction: +
(2) Denitrification: +
(3) MR test: +
(4) Vp test: −
(5) Indole formation: −
(6) Hydrogen sulfide formation: −
(7) Starch hydrolysis: −
(8) Citrate utilization: − (Simmons medium)
(9) Inorganic nitrogen source: + (nitrates, ammonium salts)
(10) Urease: −
(11) Oxidase: +
(12) Catalase: +
(13) Growth range: 20°–30° C., pH 6.5–8.5
(14) Attitude toward oxygen: aerobic
(15) O-F test: O type
(16) Formation of acid and gas from saccharide: Acid formation, −; Gas formation, − (D-glucose)
(17) Malonate utilization: −
(18) Deaminase reaction of phenylalanine: −
(19) Decarboxylase reaction: − (lysine)
(20) Arginine dihydrolase reaction: −
(21) Casein degradation: −
(22) DNA degradation: −
(23) Auxotrophy: none
(24) Utilization of carbon compounds:
   D-Glucose: +
   L-Arabinose: +
   Saccharose: +
   D-Fructose: +
   Malonate: −
   Cellobiose: +
   Ethanol: −
   D-Xylose: +
   D-Tartrate: −
   Sorbitol: +
   Citrate: −
   Lactose: +
   D-Mannitol: +
   Meso-inositol: +
   Raffinose: +
   L-Rhamnose: +
   Maltose: +
   α-Methyl-D-glucoside: +
   D-Mannose: +
   Salicin: −
   N-Acetylglucosamine: +
   Gluconate: −
   Caprate: −
   Adipate: −
   Phenylacetate: −
   Methanol: −

(25) Egg york reaction: −
(26) β-Galactosidase: +
(27) Esculin hydrolysis: +
(28) Cytochrome oxidase: +
(29) Tween degradation: − (Tween 80)
(30) 3-Ketolactose formation: −

Pseudomonas sp. KNK 003A (FERM BP-3181)

(a) Morphology:
(1) Cell size and shape: 0.5–0.7×1.2–2.5 µm, rods
(2) Cellular polymorphism: none
(3) Motility: active
(4) Sporulation: none
(5) Gram-staining: negative
(6) Colony shape: round, regular, entire, flat, smooth, shiny, semi-translucent, buff (b) Physiological Characteristics (1) Lysis by 3% KOH: +
(2) Aminopeptidase: +
(3) Oxidase: +
(4) Catalase: +
(5) Cell growth
   Anaerobic condition: −
   37°/40° C.: +/+
   pH 5.6: −
   Mac-Conkey agar: −
   SS agar: −
   Cetrimid agar: −
(6) Acid formation (O-F test)
   Glucose aerobic condition: −
   Glucose anaerobic condition: −
(7) Gas formation from glucose: −
(8) Acid formation (ASS)
   Glucose: +
   Fructose: −
   Xylose: +
(9) ONPG: −
(10) ADH: −
(11) ODC: −
(12) VP: −
(13) Indole formation: =
(14) Nitrate reduction: −
(15) Denitrification: −
(16) Phenylalanine deaminase: −
(17) Levan formation from sucrose: −
(18) Lecithinase: −
(19) Urease: −
(20) Hydrolysis
   Starch: −
   Geratin: −
   Casein: −
   DNA: −
   Tween 80: −
   Esculin: −
(21) Tyrosine degradation: −
(22) Utilization of various compounds
   Acetate: weak
   Adipate: −
   Caprate: −
   Citrate: −

Citraconate: −
Glycolate: −
Lactate: +
Levulinate: −
Malate: −
Malonate: −
Mesaconate: −
Phenylacetate: −
Suberate: −
m-Tartrate: −
D-Tartrate: −
L-Arabinose: +
Fructose: +
Glucose: +
Mannose: +
Maltose: −
Xylose: +
Saccharose: −
Trehalose: −
Ribose: −
Saccharate: −
Hydroxybutylate: −
Benzoate: −
Mannitol: +
Gluconate: +
2-Ketogluconate: +
N-Acethylglucosamine: −
L-Serine: −
L-Histidine: −
L-Valine: −

(23) Main respiratory quirtone type: ubiquinone 10

Pseudomonas sp. KNK 505 (FERM BP-3182)

(a) Morphology:
  (1) Cell size and shape: 0.5–0.7×1.2–2.5 μm, rods
  (2) Cellular polymorphism: none
  (3) Motility: active
  (4) Sporulation: none
  (5) Gram-staining: negative
  (6) Colony shape: round, regular, entire, flat, smooth, shiny, semi-translucent, buff (b) Physiological Characteristics
  (1) Lysis by 3% KOH: +
  (2) Aminopeptidase: +
  (3) Oxidase: +
  (4) Catalase: +
  (5) Cell growth
    Anaerobic condition: −
    37°/40° C.: +/+
    pH 5.6: −
    Mac-Conkey agar: −
    SS agar: −
    Cetrimid agar: −
  (6) Acid formation (O-F test)
    Glucose aerobic condition: −
    Glucose anaerobic condition: −
  (7) Gas formation from glucose: −
  (8) Acid formation (ASS)
    Glucose: +
    Fructose: −
    Xylose: +
  (9) ONPG: −
  (10) ADH: −
  (11) ODC: −
  (12) VP: −
  (13) Indote formation: −
  (14) Nitrate reduction: −
  (15) Denitrification: −
  (16) Phenylalanine deaminase: −
  (17) Levan formation from sucrose: −
  (18) Lecithinase: −
  (19) Urease: −
  (20) Hydrolysis
    Starch: −
    Geratin: −
    Casein: −
    DNA: −
    Tween 80: −
    Esculin: −
  (21) Tyrosine degradation: −
  (22) Utilization of various compounds
    Acetate: weak
    Adipate: −
    Caprate: −
    Citrate: −
    Citraconate: −
    Glycolate: −
    Lactate: +
    Levulinate: −
    Malate: −
    Malonate: −
    Mesaconate: −
    Phenylacetate: −
    Suberate: −
    m-Tartrate: −
    D-Tartrate: −
    L-Arabinose: +
    Fructose: +
    Glucose: +
    Mannose: +
    Maltose: −
    Xylose: +
    Saccharose: −
    Trehalose: −
    Ribose: −
    Saccharate: −
    Hydroxybutylate: −
    Benzoate: −
    Mannitol: +
    Gluconate: +
    2-Ketogluconate: +
    N-Acethylglucosamine: −
    L-Serine: −
    L-Histidine: −
    L-Valine: −
  (23) Main respiratory quinone type: ubiquinone 10

To obtain a gene from these strains, which is related to an enzyme capable of converting D-N-carbamoyl-α-amino acids by removal of their carbamoyl groups into the corresponding D-α-amino acids, usually, genetic DNA is extracted from the chromosome of microorganisms according to the conventional procedure, after which a DNA fragment containing the desired gene is obtained and subjected to an analysis for its base sequence. Moreover, microorganisms which produce an enzyme capable of converting D-N-carbamoyl-α-amino acids by removal of their carbamoyl groups into the corresponding D-α-amino acids, as well as transformed microorganisms into which this enzyme gene has been incorporated, are cultivated, and the produced enzyme is purified, after which the molecular weight of its protein is determined and the amino acid sequence in the vicinity of its amino terminus is determined by a gas-phase protein sequencer or the like. Then, this DNA base sequence is compared with the amino terminal sequence of the protein, so that the initiation site foI genetic translation into a protein, of the base sequence portion encoding an enzyme protein which is related to removal of carbamoyl groups is determined, and taking into consideration the relation to the molecular weight of the protein, it is confirmed that the enzyme protein is encoded in the gene portion extending from this site to the termination codon, thereby verifying the desired gene (Molecular Cloning, A Laboratory Manual, 2nd Ed., Cold Spring Harbor Laboratory Press, Chaps. 4 and 13). According to these procedures, DNA fragments of SEQ ID Nos. 1 and 2 in the accompanying Sequence Listing were obtained from the strains *Agrobacterium radiobacter* KNK 712 and Pseudomonas sp. KNK 003A. The thus-obtained gene encoding the above enzyme and/or DNA fragment containing this gene are equivalent to DNA fragments having another base sequence which encodes an amino acid sequence corresponding to the above gene and/or DNA fragment because one amino acid usually corresponds to a plurality of base codons, and this fact is obvious.

As the vector used in the present invention, plasmids, phages, or derivatives thereof can be used, which are derived from microorganisms and can be autonomously grown in cells of a bacteria belonging to the genus Escherichia, Pseudomonas, Flavobacterium, Bacillus, Serratia, Croynebacterium, or Brevibacterium. For example, host-vector systems described in "Guidelines on Recombinant DNA Experiments" (Ed., the Life Science Section of the Research Development Office in the Science and Technology Agency: revised on Sep. 16, 1987), page 55, can be used. Moreover, vectors, which have been modified to have a strong structural promoter for the purpose of increasing the amount of enzyme to be produced, can also be used.

The preparation of a recombinant comprising a vector DNA and a gene-containing DNA fragment can be conducted by freely using the known in vitro recombinant DNA technique. The in vitro DNA recombination is usually conducted by cleavage and ligation (ligase reaction) of a vector DNA and a donor DNA containing the desired gene (e.g., see the specifications of Japanese Patent Application No. 56-211908 and U.S. Pat. No. 4,237,224). Many kinds of recombinant DNA, in addition to the desired recombinant DNA, are produced by ligase reaction, and therefore, for the purpose of selectively obtaining the desired recombinant DNA, microorganisms belonging to the genus Escherichia, Pseudomonas, Flavobacterium, Bacillus, Serratia, Croynebacterium, or Brevibacterium may be directly transformed with a ligase reaction mixture, and the resulting transformants on which the inherited character from the genetic information of the desired gene has been conferred may be selectively separated, and the desired recombinant DNA may be extracted and isolated from their cultured bacterial cells.

For example, the recombinant can also be obtained without direct transformation of bacterial species belonging to any one of the above genera; that is, the desired gene is once cloned in a host vector system using other microorganisms, such as *Escherichia coli*, after which recombinant DNA with an appropriate vector is in vitro produced, and then the above bacterial species are transformed, followed by selective separation of transformants in the same manner as described above.

The description of the following documents can be widely applied to the production of recombinants: the specification of U.S. Pat. No. 4,237,224 to S.N. Cohen, et al.; "Idenshisousa Jikken-hou (Experimental Method of Gene Manipulation)" [Ed., Yasuyuki Takagi, Kohdansha Scientific (1980)]; Method in Enzymdogy, 68, Recombinant DNA [Ed., Ray Mv, Academic Press (1979)]; the specification of Japanese Patent Application No. 56-211908, etc.

In the case of *Escherichia coli* transformed with various kinds of recombinant DNA, a method for selecting, from the transformed strains, particular transformed strains which have the desired gene, i.e., the gene of a particular D-N-carbamoyl-α-amino acid amidohydrolase, and in which that gene has been expressed, is conducted as follows: colonies of the transformed strains are first grown on the plate containing a selection marker, such as ampicillin. Then, various colonies of these transformed strains having the recombinant DNA are collected and suspended in physiological saline, after which this suspension is inoculated on the minimum liquid medium containing a particular D-N-carbamoyl-α-amino acid as a sole nitrogen source. On this medium, only transformed strains capable of utilizing the D-N-carbamoyl-α-amino acid, i.e., transformed strains on which D-N-carbamoyl-α-amino acid amidohydrolase activity has been now conferred, can be grown. The culture solution thus obtained is inoculated on the above minimum medium, and such an operation is repeated, resulting in an enrichment of the desired transformed strains. From this enriched culture solution, bacterial cells are separated according to the conventional method, and the separated transformed strains are cultivated to make a bacterial reaction with a D-N-carbamoyl-α-amino acid as a substrate, whereby the transformed strains containing the desired gene can be obtained by confirming the production of a D-α-amino acid.

From the transformed strains thus obtained, recombinant DNA is extracted according to the conventional method, such as a method using alkali denaturation (see Molecular Cloning A Laboratory Manual, 2nd Ed., Cold Spring Harbor Laboratory Press, Chap. 1); the structural gene of the desired enzyme in the DNA fragments containing the cloned desired gene is subcloned and unnecessary DNA is removed; recombinant DNA modified to have a strong promoter is prepared in a vector; the above host bacteria are transformed therewith; and the resulting transformed strains are used to increase the amount of the desired enzyme to be produced.

The introduced character of the recombinant DNA can be expressed by cultivating the transformed strains on a conventional nutrient medium. In cases where the character from the gene DNA or vector DNA is conferred on the recombinant DNA, any drug may be supplemented to the medium depending upon that character.

To take the transformed strains thus obtained, as a source of enzyme supply, culture may be prepared with the use of a conventional medium, and when necessary, it is also possible to conduct a treatment for enzyme induction, such as an addition of hydantoin compounds, D-N-carbamoyl-α-amino acids, isopropyl-1-thio-β-D-galactosides (IPTG), or the like, and a temperature increase.

Usually, the medium used for cultivating the transformed strains may be a conventional medium containing carbon sources, nitrogen sources, and inorganic ions. If organic tracenutrients, such as vitamines and amino acids, are added thereto, satisfactory results may be obtained in may cases. As the carbon sources, carbohydrates, such as glucose and sucrose; organic acids, such as acetic acid; alcohols, and the like, are conveniently used. As the nitrogen sources, ammonia gas, ammonia water, ammonium salts, and the like, are used. As the inorganic ions, phosphate ion, magnesium ion, potassium ion, iron ion, and the like, may be used.

If culture is prepared under aerobic conditions for 1–10 days, while adjusting the pH and temperature to an appropriate range of 4°–8° and 25°–45° C., respectively, it is possible to obtain desirable results.

Examples of the embodiments acting as an enzyme produced by the transformed strains include culture solutions of the transformed strains, bacterial cells, treated bacterial cells, enzymes extracted from bacterial cells, immobilized bacterial cells, and the like.

As the bacterial cells, any of the culture solution as it is after completion of cultivation, bacterial cells separated from the culture solution, washed bacterial cells, and the like, can be used. As the treated bacterial cells, lyophilized bacterial cells, acetone-dried bacterial cells, bacterial cells brought into contact with toluene or detergents, lysozyme-treated bacterial cells, bacterial cells exposed to ultrasonic waves, mechanically ground bacterial cells, and the like, can be used, as well as enzyme extracts having the enzyme activity to convert D-N-carbamoyl-α-amino acids obtained from these treated bacterial cells, by removal of their carbamoyl groups into the corresponding D-α-amino-acids; these immobilized bacterial cells; insolubilized treated bacterial cells; enzyme proteins fixed on a support for immobilization (e.g., anion exchange resin), and the like. For an immobilization method, for example, it is possible to make reference to the specification of Japanese Patent Laid-open Publication No. 63-185382.

As the support used for immobilization, suited are phenol-formaldehyde anion exchange resins, such as Duolite A568 or DS17186 (Rohm & Haas Co.: registered trade mark); and various anion exchange resins containing various amines, ammonium salts, or functional groups of the diethanolamine type, for example, polystylene resins, such as Amberlite IRA935, IRA945, IRA901 (Rohm & Haas Co.: registered trade mark), Lewatit OC1037 (Bayer A.G.: registered trade mark), and Diaion EX-05 (Mitsubishi Chemical Industries Ltd.: registered trade mark). Other supports, such as DEAE-cellulose, can also be used.

Further, to obtain stronger and more stable adsorption of enzymes, usually, cross-linking agents are used, the preferred examples thereof being glutaraldehyde. As the enzyme to be used, not only purified enzymes, but also those with different degrees of purification, such as partially purified enzymes, suspensions of disintegrated bacterial cells, and cell-free extracts, can be used.

The preparation of immobilized enzymes can be conducted by using an enzyme solution and the conventional method in which, for example, enzymes are adsorbed on a support, followed by cross-linking treatment.

D-N-carbamoyl-α-amino acids, which are used as a substrate of the enzymatic reaction of the present invention, can be represented by the formula: R—CH(NHCONH$_2$)—COOH, and as a practical embodiment, in cases where the enzyme used has strict stereoselectivity to D-N-carbamoyl-α-amino acids, it can be used as the D-form or a mixture of the D- and L-forms. Moreover, in cases where the stereoselectivity is not strict because enzymes also act on L-carbamoyl amino acids, or where enzymes are used as an enzyme mixture also acting on the L-form thereof, it is preferred that only enzymes of the D-form are used to produce α-amino acids of the D-form.

The substituent R can beselected in a wide range, as described in the specifications of Japanese Patent Publication Nos. 57-18793, 63-20520, and 1-48758; in particular, to provide industrially useful compounds, such as intermediates of drugs, it is preferred that R is phenyl, phenyl substituted with hydroxy, alkyl, substituted alkyl, aralkyl, or thienyl. In the case of phenyl substituted with hydroxy, the number of hydroxy is one or more, and they may be attached at any of o-, m-, and p-positions, with the typical example thereof being p-hydroxyphenyl. The alkyl group is such a group of 1–4 carbon atoms that the corresponding amino acid becomes D-alanine, D-valine, D-leucine, D-isoleucine, or the like. The substituted alkyl group is such an alkyl having 1–4 carbon atoms substituted with hydroxy, alkylthio, carboxyl, amino, phenyl, phenyl substituted with hydroxy, amido, or the like, that the corresponding amino acid becomes D-serine, D-threonine, D-methionine, D-cysteine, D-asparagine, D-glutamine, D-tyrosine, D-tryptophane, D-aspartic acid, D-glutamic acid, D-histidine, D-lysine, D-arginine, D-citrulline, or the like. The aralkyl group is such a group having 7–8 carbon atoms, for example, benzyl or phenthyl, that the corresponding amino acid becomes D-phenylalanine or the like.

As the aqueous medium, those containing water, buffers, or organic solvents, such as ethanol, can be used. Further, when necessary, nutrients required for the growth of microorganisms, antioxidants, detergents, coenzymes, hydroxylamines, metals, or the like, can also be added to the aqueous medium.

In cases where, while cultivating the bacterial cells of the above microorganisms in a water-soluble medium, the bacterial cells are brought into contact with a particular D-N-carbamoyl-α-amino acid, an aqueous medium containing not only a D-N-α-amino acid but also nutrients required for the growth of microorganisms, such as carbon sources, nitrogen sources, and inorganic ions, is used. Further, if organic tracenutrients, such as vitamines and amino acids, are added thereto, satisfactory results can be obtained in many cases. As the carbon sources, carbohydrates, such as glucose and sucrose; organic acids, such as acetic acid; alcohols, and the like, are conveniently used. As the nitrogen sources, ammonia gas, ammonia water, ammonium salts, and the like, are used. As the inorganic ions, phosphate ion, magnesium ion, potassium ion, iron ion, and the like, may be used.

The cultivation is conducted under aerobic conditions, while adjusting the pH and temperature to an appropriate range of 4°–8° and 25°–45° C., respectively. If the cultivation is conducted for 1–10 days, D-N-carbamoyl-α-amino acids can be converted into only D-α-amino acids with high efficiency.

To the contrary, in cases where the culture-solution of the above microorganisms is allowed as it is, to react with cultivated bacterial cells, treated bacterial cells, enzyme extracts, immobilized bacterial cells, insolubilized bacterial cells, or fixed enzyme proteins, in an aqueous medium containing a particular D-N-carbamoyl-α-amino acid dissolved or suspended, the reaction mixture may be allowed to stand for some time or stirred, while maintaining at an appropriate temperature of 10°–80° C. and pH of 4–9.5. Thus, if 5–100 hours have run their course, the corresponding D-α-amino acid is produced in large quantities and enriched in the aqueous-medium. Moreover, the D-N-carbamoyl-α-amino acid may be added in separate portions with the progress of reaction. The produced D-α-amino acid can be separated and purified by a conventional separation method.

The D-α-amino acid thus obtained can be represented by the formula: R—CHNH$_2$COOH (R is as defined above).

EXAMPLES

The following will describe the embodiments of the present invention. The D-α-amino acid produced was

Example 1

Preparation of recombinant DNA comprising chromosome DNA from *Agrobacterium radiobacter* KNK 712 (FERM BP-1900) and vector DNA:

*Agrobacterium radiobacter* KNK 712 (FERM BP-1900) was cultivated in 2 liters of L-broth (10 g of peptone/liter, 5 g of yeast extract/liter, 5 g of sodium chloride/liter; pH 7.0) at 33° C. for 27 hours, after which cultures were harvested to give 20 g of bacterial cells. From the bacterial cells obtained, chromosome DNA was extracted according to the Marmur method. To 250 μg of this chromosome DNA, 2 U of Sau3AI were added, and allowed to react at 37° C. for 30 minutes, thereby causing partial digestion. From the partially digested DNA, 4–9 kbp DNA fragments were obtained by agarose gel electrophoresis. On the other hand, plasmid pUC 18 was completely digested with BamHI, and ligated with T4 DNA ligase to the above-obtained DNA fragments from chromosome, resulting in a mixed solution of various recombinant plasmids.

Example 2

Selection of plasmid derived from *Agrobacterium radiobacter* KNK 712 (FERM BP-1900) and containing gene related to conversion of D-N-carbamoyl-α-amino acid into the corresponding D-α-amino acid:

Using the mixed plasmid solution of Example 1, *Escherichia coli* JM 109 was transformed according to the conventional method. This was inoculated on the medium of Table 1, containing ampicillin as a selection marker.

TABLE 1

| | |
|---|---|
| Polypeptone | 10 g |
| Yeast extract | 0.5 g |
| Sodium chloride | 0.5 g |
| Ampicillin | 100 mg |
| Ager | 15 g |
| Water was added to the volume of 1 liter (pH 7.0). | |

The grown colonies were collected and inoculated into the liquid medium of Table 2, containing D-N-carbamoyl-alanine as a sole nitrogen source, followed by cultivation.

TABLE 2

| | |
|---|---|
| $Na_2HPO_4$ | 6 g |
| $KH_2PO_4$ | 3 g |
| NaCl | 0.5 g |
| $MgSO_4$ | 0.12 g |
| $CaCl_2$ | 11 mg |
| Glucose | 2 g |
| Ampicillin | 50 mg |
| Thiamin | 1 mg |
| D-N-Carbamoyl-alanine | 1 g |
| Water was added to the volume of 1 liter (pH 7.0). | |

Only the transformed strains expressing the desired gene can be grown on the medium of Table 2 by utilizing D-N-carbamoyl-alanine as a nitrogen source. The culture solution in the medium of Table 2 was inoculated into the same medium as used above, and this operation was repeated for enrichment of the desired transformed strains. From the enriched culture solution, the transformed strains were purely separated with the medium of Table 1. These purely separated cells were inoculated into 10 ml of L-broth (10 g of peptone/liter, 5 g of yeast extract/liter, 5 g of sodium chloride/liter; pH 7.0) containing 100 mg/liter of ampicillin, and incubated at 37° C. for 16 hours, after which 1 ml of the culture solution was harvested and the supernatant was removed therefrom, followed by suspension of the bacterial cells in 0.5 ml of substrate solution (0.5% D-N-carbamoyl-parahydroxyphenylglycine, 0.05% Triton X-100, 0.1M phosphate buffer (hereinafter referred to as KPB); pH 7.0) and allowing to react at 37° C. for 3 hours. This reaction mixture was spotted on TLC and developed, followed by staining with ninhydrin, resulting in a spot of D-parahydroxyphenylglycine which was in agreement with the standard. From this fact, it was confirmed that the transformed strains purely separated have a plasmid containing a gene related to the desired enzyme. The plasmid contained in these strains was named pAHD 101.

Then, from the above transformed strains, pAHD 101 was prepared in large quantities according to the alkali denaturation method, followed by mapping, which reveled that it had the structure shown in FIG. 1.

*Escherichia coli* JM 109 transformed with pAHD 101 was named *Escherichia coli* JM 109 pAHD 101.

Example 3

Selection of plasmid derived from Pseudomonas sp. KNK 003A (FERM BP-3181) and containing gene related to conversion of D-N-carbamoyl-α-amino acid into the corresponding D-α-amino acid:

In the same manner as described in Example 1, a mixed solution of various recombinant plasmids formed from chromosome DNA fragments of Pseudomonas sp. KNK 003A (FERM BP-3181) and plasmid pUC18 was obtained. Using this mixed solution, *Escherichia coli* JM 109 was transformed according to the conventional method. From these various transformed strains, particular transformed strains having a plasmid which contains a gene related to an enzyme capable of converting D-N-carbamoyl-α-amino acids into the corresponding D-α-amino acids were obtained in the same manner as described in Example 2, except that the liquid medium of Table 2, containing 100 mg/liter of IPTG, was used in place of the liquid medium of Table 2. The plasmid contained in these strains was named pPHD 301.

Then, from the above transformed strains, pPHD 301 was prepared in large quantities, followed by mapping, which revealed that it had the structure shown in FIG. 2.

*Escherichia coli* JM 109 transformed with pPHD 301 was named *Escherichia coli* JM 109 pPHD 301.

Example 4

Subcloning of pAHD 101

The pAHD 101 obtained in Example 2 was completely digested with SmaI and EcoRI, and a 2.7 kbp SmaI-EcoRI fragment was obtained by agarose gel electrophoresis. On the other hand, plasmid pUC 19 was completely digested with SmaI and EcoRI, and ligated with T4 DNA ligase to the SmaI-EcoRI fragment of pAHD 101, after which *Escherichia coli* JM 109 was transformed with this ligated plasmid and the transformed strains were cultivated on an L-medium (1% peptone, 0.5% yeast extract, 0.5% sodium chloride, 1.5% agar; pH 7.0) containing isopropyl-1-thio-β-D-galactoside (IPTG), 5-chloro-4-bromo-3-indolyl-β-D-galactose (Xgal) and ampicillin.

The plasmid corresponding to pUC 19 containing the SmaI-EcoRI fragment of pAHD 101 formed white colonies without exhibiting blue color, and therefore, these white colonies were selected. To confirm that these selected bacteria have the desired enzyme activity, they were inoculated into 10 ml of L-broth (1% peptone, 0.5% yeast extract, 0.5% sodium chloride) containing 100 mg/liter of ampicillin after cultivation of which 1 ml of the culture solution was harvested and the supernatant was removed therefrom, and the bacterial cells were suspended in 0.5 ml of substrate solution (0.5% D-N-carbamoyl-parahydroxy-phenylglycine, 0.05% Triton X-100, 0.1M phosphate buffer; pH 7.0), followed by reaction at 37° C. for 3 hours. This reaction mixture was spotted on TLC and developed, followed by staining with ninhydrin, resulting in a spot of D-parahydroxyphenylglycine which was in agreement with the standard. The plasmid contained in these transformed strains was named pAD 107.

Then, the plasmid pAD 107 was prepared and partially hydrolyzed with SalI, followed by agarose gel electrophoresis to give a 4.5 kbp fragment containing the pUC 19 portion. This fragment was circularized with T4 DNA ligase, and this plasmid was used to transform *Escherichia coli* JM 109. The trasformed strains were obtained from the L-medium containing ampicillin and bacterial reaction was conducted in the same manner as described above, thereby obtaining transformed strains having the ability to convert D-N-carbamoyl-parahydroxyphenylglycine into D-parahydroxyphenylglycine. The plasmid contained in these transformed strains was named pAD 108. The pAD 108 was prepared form the above transformed strains, followed by mapping, which revealed that it had the structure shown in FIG. 3.

*Escherichia coli* JM 109 transformed with pAD 108 was named *Escherichia coli* JM 109 pAD 108. The accession number given from the Fermentation Research Institute was FERM BP-3184.

Example 5

Subcloning of pPHD 301

The pPHD 301 obtained in Example 3 was completely digested with AccI, and a 5.2 kbp fragment containing the pUC 18 portion was obtained by agarose gel electrophoresis. This fragment was circularized with T4 DNA ligase, and this plasmid was used to transform *Escherichia coli* JM 109. The trasformed strains were obtained from an L-medium containing ampicillin and bacterial reaction was conducted in the same manner as described in Example 4, thereby obtaining transformed strains having the ability to convert D-N-carbamoyl-parahydroxyphenylglycine into D-parahydroxyphenylglycine. The plasmid contained in these transformed strains was named pPD 302.

Then, the plasmid pPD 302 was prepared and completely digested with SphI and AccI, after which a 1.8 kbp SphI-AccI fragment was obtained by agarose gel electrophoresis. On the other hand, plasmid pUC 19 was completely digested with SphI and AccI, and ligated with T4 DNA ligase to the SphI-AccI fragment of pPD 302, after which *Escherichia coli* JM 109 was transformed with this ligated plasmid. The trasformed strains were obtained from an L-medium containing ampicillin, and bacterial reaction was conducted in the same manner as described in Example 4, thereby obtaining transformed strains having the ability to convert D-N-carbamoyl-parahydroxyphenylglycine into D-parahydroxyphenylglycine. The plasmid contained in these transformed strains was named pPD 304. The plasmid pPD 304 was prepared from the above transformed strains, followed by mapping, which revealed that it had the structure shown in FIG. 4.

*Escherichia coli* JM 109 transformed with pPD 304 was named *Escherichia coli* JM 109 pPD 304. The accession number given from the Fermentation Research Institute was FERM BP-3183.

Example 6

Conversion of D-N-carbamoyl-α-amino acid into D-α-amino acid with enzyme obtained from transformed strains:

Using the plasmid pAD 108 obtained in Example 4, *Escherichia coli* JM 109 was transformed. This strain was cultivated in L-broth containing 100 μg/ml of ampicillin and 100 μg/ml of IPTG at 37° C. for 16 hours. From 100 ml of this culture solution, bacterial cells were harvested and then suspended in 0.1M KPB (pH 7.0) to the volume of 10 ml. This was subjected to ultrasonication while cooling with ice, followed by centrifugation to give the supernatant as a crude enzyme solution. Using this crude enzyme solution, reaction was conducted with various kinds of D-N-carbamoyl-α-amino acid shown in Table 3 as a substrate. To 2 ml of 40 mM D-N-carbamoyl-α-amino acid (Table 3) and 0.2M KPB (pH 7.0), 100 μl of the above crude enzyme solution were added, thereby allowing to react at 40° C. for 20 minutes, and the amount of D-α-amino acid produced was determined. The results are shown in Table 3. Moreover, there was a 10-fold improvement in the specific activity of a D-N-carbamoyl-α-amino acid amidohydrolase obtained from JM 109 pAD 108 at this time as compared with a crude enzyme solution from *Agrobacterium radiobacter* KNK 712 (FERM BP-1900).

Example 7

Conversion of D-N-carbamoyl-α-amino acid into D-α-amino acid with enzyme obtained from transformed strains:

Using the plasmid pPD 304 obtained in Example 5, *Escherichia coli* JM 109 was transformed. From this strain, a crude enzyme solution was obtained in the same manner as described in Example 6. Using this crude enzyme solution, reaction was conducted in the same manner as described in Example 6. The results are shown in Table 3. There was a 40-fold improvement in the specific activity of a D-N-carbamoyl-α-amino acid amidohydrolase obtained from JM 109 pPD 304 at this time as compared with a crude enzyme solution from Pseudomonas sp. KNK 003A (FERM BP-3181).

Example 8

Conversion of D-N-narbamoyl-parahydroxyphenyl-glycine into D-parahydroxyphenylglycine with enzyme obtained from transformed strains:

Using the plasmid pAD 108 obtained in Example 4, *Escherichia coli* JM 109 was transformed. This strain was cultivated in the same manner as described in Example 6. From 100 ml of the culture solution, bacterial cells were harvested, and washed with 0.1M KPB (pH 7.0), after which they were suspended in 100 ml of 5% D-N-carbamoyl-parahydroxyphenylglycine, 0.05% Triton X-100, and 0.1M KPB (pH 7.0), followed by stirring at 40° C. for 20 hours to cause reaction. The reaction mixture thus obtained was subjected to centrifugation at 6000 rpm for 10 minutes to remove the bacterial cells, and pH was decreased to 2.7 by addition of concentrated hydrochloric acid, followed by adsorption on the cation exchange resin IR-120B (H⁺ type) and elution with 5% $NH_4OH$. Then, the eluates were desalinized with IRC-84 (H⁺ type) and decolorized with an AF resin. The decolorized solution was concentrated to allow crystallization, and the deposited crystals were recrystallized from water to give 3.8 g of white powder. These crystals exhibited the specific rotation $[\alpha]_D^{20}=-158$ (C=1, 1N HCl), and gave a single spot on TLC, and the IR spectrum thereof was in agreement with that of the D-parahydroxyphenylglycine standard.

Example 9

Preparation of fixed D-N-carbamoyl-α-amino acid amidohydrolase:

After 200 ml of the culture solution obtained, in the same manner as described in Example 6, from the strains of Escherichia coli JM 109 transformed with pAD 108 was harvested, they were washed with 0.1M KPB (pH 7.0), and suspended in 20 ml of 0.1M KPB (pH 7.0), followed by ultrasonication of the bacterial cells. This suspension of disintegrated bacterial cells was subjected to centrifugation at 12000 rpm for 20 minutes to give the supernatant as a crude enzyme solution. To this crude enzyme solution, 2 g of anion exchange resin Duolite A-568 equilibrated with 0.1M KPB (pH 7.0) were added, and stirred at 4° C. for 15 hours to make the enzyme adsorbed thereon. To this solution, glutaraldehyde was added to have a final concentration of 0.1%, and stirred for 1 hour, followed by cross-linking treatment, after which the resin was collected by filtration and washed with 0.1M KPB, resulting in 2 g of fixed D-N-carbamoyl-α-amino acid amidohydrolase.

Example 10

Conversion of D-N-carbamoyl-parahydroxyphenylglycine into D-parahydroxyphenylglycine with immobilized enzyme:

Two grams of immobilized D-N-carbamoyl-α-amino acid amidohydrolase obtained in Example 9 were added to 100 ml of 2% D-N-carbamoyl-parahydroxyphenylglycine and 0.1M KPB (pH 7.0), and stirred at 40° C. for 20 hours, while maintaining the pH at 7.0 by addition of 1N HCl, thereby causing reaction. After the reaction, the mixture was allowed to stand, and the reaction mixture was collected by suction, after which the produced amino acid was purified in the same manner as described in Example 8 to give 1.5 g of D-parahydroxyphenylglycine.

TABLE 3

| Reaction substrate | Amino acid produced | Amount of amino acid produced (mmol/liter) | | |
| --- | --- | --- | --- | --- |
| | | JM 109 pAD 108 | JM 109 pPD 304 | JM 109 |
| D-N-Carbamoyl-parahydroxyphenylglycine | D-Parahydroxyphenylglycine | 9.5 | 0.14 | 0 |
| D-N-Carbamoyl-phenylglycine | D-Phenylglycine | 9.7 | 0.06 | 0 |
| D-N-Carbamoyl-homophenylalanine | D-Homophenylalanine | 3.9 | 0.78 | 0 |
| D-N-Carbamoyl-phenylalanine | D-Phenylalanine | 4.2 | 0.98 | 0 |
| D-N-Carbamoyl-leucine | D-Leucine | 6.4 | 1.37 | 0 |
| D-N-Carbamoyl-valine | D-Valine | 6.6 | 0.98 | 0 |
| D-N-Carbamoyl-alanine | D-Alanine | 7.0 | 1.56 | 0 |

Example 11

Analysis of DNA base sequence for the gene of enzyme derived from Agrobacterium radiobacter KNK 712 (FERM BP-1900) and capable of converting D-N-carbamoyl-α-amino acid into the corresponding D-α-amino acid:

The plasmid pAD 108 containing the gene of a D-N-carbamoyl-α-amino acid amidohydrolase (hereinafter referred to as amidohydrolase) derived from Agrobacterium radiobacter KNK 712 (FERM BP-1900) was digested with restriction endonucleases EcoRI and HindIII (manufactured by Takara Shuzo Co., Ltd.), and a 1.8 kb DNA fragment was separated for preparation by agarose gel electrophoresis. This fragment was digested with various restriction endonucleases, and ligated with T4-DNA ligase (manufactured by Takara Shuzo Co., Ltd.) to M13mp18 or M13mp19, after which Escherichia coli JM 109 was infected therewith, resulting in the formation of a plaque. This single plaque was inoculated into 1.5 ml of 2YT medium (16 g/l of bactotrypton (Difco Co.), 10 g/l of yeast extract (Difco Co.), and 5 g/l of NaCl) into which 1% JM 109 overnight cultured broth had been inoculated, and subjected to shaking culture at 37° C. for 5 hours. After centrifugation, 200 μl of 20% polyethyleneglycol 6000 and 2.5M NaCl solution were added to the supernatant, and allowed to stand at room temperature for 15 minutes, after which phage particles were recovered as a precipitate by centrifugation. This was dissolved in 100 μl of TE solution [10 mM Tris HCl (pH 8.0), 1 mM EDTA], and extracted with 50 μl of phenol (saturated with TE solution), after which 10 μl 1 of 3M sodium acetate solution and 250 μl of ethanol were added and allowed to stand overnight at −20° C., followed by centrifugation. After drying, the precipitate was dissolved in 50 μl of TE solution. Then, 7 μl of this solution was used for reaction, electrophoresis, and autoradiography with the aid of a DNA sequence kit (manufactured by United States Biochemical Corp.) using SEQUENASE (registered trademark) ver. 2, according to its instruction manual. From the results obtained, the DNA base sequence of amidohydrolase gene for the strain KNK 712 was determined as shown by SEQ ID No. 1 in the accompanying Sequence Listing.

Example 12

Analysis of DNA base sequence for the gene of enzyme derived from Pseudomonas sp. KNK 003A (FERM BP-3181) and capable of converting D-N-carbamoyl-α-amino acid into the corresponding D-α-amino acid:

The plasmid pPD 304 containing amidohydrolase gene derived from the strain KNK 003A was digested with restriction endonucleases BamHI and HindIII (manufactured by Takara Shuzo Co., Ltd.), and a 1.8 kb DNA fragment was separated for preparation by agarose gel electrophoresis. This fragment was digested with various restriction endonucleases, and ligated with T4-DNA ligase (Takara Shuzo Co., Ltd.) to M13mp18 or M13mp19, after which *Escherichia coli* JM 109 was infected therewith, resulting in the formation of a plaque. This single plaque was inoculated into 1.5 ml of 2YT medium (16 g/l bactotrypton (Difco Co.), 10 g/l yeast extract (Difco Co.), and 5 g/l NaCl) into which 1% JM 109 overnight cultured broth had been inoculated, and subjected to shaking culture at 37° C. for 5 hours. After centrifugation, 200 μl of 20% polyethyleneglycol 6000 and 2.5M NaCl solution were added to the supernatant, and allowed to stand at room temperature for 15 minutes, after which phage particles were recovered as a precipitate by centrifugation. This was dissolved in 100 μl of TE solution [10 mM Tris HCl (pH 8.0), 1 mM EDTA], and extracted with 50 μl of phenol (saturated with TE solution), after which 10 μl 1 of 3M sodium acetate solution and 250 μl of ethanol were added thereto, and allowed to stand overnight at −20° C., followed by centrifugation. After drying, the precipitate was dissolved in 50 μl of TE solution. Then, 7 μl of this solution was used for reaction, electrophoresis, and autoradiography with the aid of a DNA sequence kit (manufactured by United States Biochemical Corp.) using SEQUENASE (registered trade mark) ver. 2, according to its instruction mannual. From the results obtained, the DNA base sequence of amidohydrolase gene derived from the strain KNK 003A was determined as shown by SEQ ID No. 2 in the accompanying Sequence Listing.

Example 13

Purification of D-N-carbamoyl-α-amidohydrolase derived from *Agrobacterium radiobacter* KNK 712 (FERM BP- 900):

*Agrobacterium radiobacter* KNK 712 (FERM BP-1900) was cultivated in the medium of Table 4 at 33° C. for 25 hours.

TABLE 4

| | |
|---|---|
| Glycerin | 25 g |
| Sucrose | 5 g |
| $KH_2PO_4$ | 5 g |
| $Na_2HPO_4$ | 5 g |
| $MgSO_4.7H_2O$ | 1 g |
| $MnCl_2.4H_2O$ | 10 mg |
| Yeast extract | 4 g |
| Urea | 2 g |
| D-N-carbamoyl-P-hydroxyphenylglycine | 1 g |
| Water was added to the volume of 1 liter (pH 6.5). | |

Twenty one liters of this culture solution were harvested and the bacterial cells were ultrasonicated. After removal of the reside by centrifugation, nucleic acids were removed by protamine sulfate treatment (0.1 mg/mg of protein). The centrifuged supernatant was subjected to heat treatment at 50° C. for 20 minutes, and after removal of the precipitate, protein was precipitated by addition of ammonium sulfate, and a protein fraction having activity and being precipitated with 15% to 35% saturated ammonium sulfate was recovered. This fraction was dissolved and subjected to HPLC using DEAE-5pw column (manufactured by Toso Co., Ltd.), followed by elution with a concentration gradient of NaCl and recovered active fractions. At this stage, in comparison with a suspension of disintegrated bacterial cells, there was about 20-fold increase in the specific activity of amidohydrolase. When this fraction was analyzed by SDS-polyacrylamide gel electrophoresis, this amidohydrolase migrated near to the position corresponding to the molecular weight of about 35,000.

Example 14

Determination of amino acid sequence around protein amino terminus of D-N-carbamoyl-α-amino acid amidohydrolase derived from *Agrobacterium radiobacter* KNK 712 (FERM BP- 1900):

A purified amidohydrolase preparation produced by *Agrobacterium radiobacter* KNK 712 (FERM BP-1900) obtained in Example 13 was charged in a reverse-phase HPLC column (AP-303; manufactured by YMC Co.), and eluted with a concentration gradient of a cetonitrile. This fraction containing the amidohydrolase was charged for analysis in a gas-phase protein sequencer (manufactured by Applied Biosystems Co., Ltd.), and it was found that the amidohydrolase is a protein having a sequence in the amino terminus portion, which consists of 1st to 20th amino acids of SEQ ID No. 1 in the accompanying Sequence Listing.

Example 15

Purification of D-N-carbamoyl-α-amino acid amidohydrolase derived from Pseudomonas sp. KNK 003A (FERM BP-3181):

Pseudomonas sp. KNK 003A (FERM BP-3181) was cultivated in the medium of Table 5 at 45° C. for 3 days.

TABLE 5

| | |
|---|---|
| Glycerin | 10 g |
| Glucose | 5 g |
| $KH_2PO_4$ | 3.5 g |
| $Na_2HPO_4$ | 3.5 g |
| $MgSO_4.7H_2O$ | 0.5 g |
| $MnCl_2.4H_2O$ | 20 mg |
| $FeSO_4$ | 10 mg |
| $CaCO_3$ | 1 g |
| Meat extract | 2 g |
| Extract ehlrich | 2 g |
| Polypeptone | 2 g |
| D-N-carbamoylalanine | 1 g |
| Water was added to the volume of 1 liter (pH 7.0). | |

Twenty six liters of this culture solution were harvested, and in the same manner as described in Example 13, the following operations were conducted: ultrasonication of the bacterial cells; removal of nucleic acids by protamine sulfate treatment; heat treatment (65° C., 20 min); fractionation by ammonium sulfate precipitation (separation of protein fractions having amidohydrolase activity and being precipitated with 50% to 70% saturated ammonium sulfate); and HPLC using DEAE-5pw column. These active fractions was allowed to adsorb in a Biogel-HT (Bio-Rad Laboratories Co., Ltd.) column, and eluted with a concentration gradient of ammonium sulfate, after which the active fractions were concentrated and subjected to gel filtration using a Sephacryl S-300 (Pharmacia LKB Biotechnology Co., Ltd.) column.

Then, when isoelectric focusing (pH 4 to 6.5) was conducted, the above amidohydrolase migrated near to the position at pH 5.7, and the gel of this band portion having activity was cut out, from which protein was extracted. At this stage, in comparison with a suspension of the disintegrated bacterial cells, there was about 100-fold increase in the specific activity of amidohydrolase. When this sample was analyzed by SDS-polyacrylamide gel electrophoresis, amidohydrolase migrated near to the position corresponding to the molecular weight of about 38,000. Moreover, when this sample was subjected to gel filtration using a Sephacryl

19

S-200 column, it was eluted at the position corresponding to the molecular weight of about 67,000.

Example 16

Determination of amino acid sequence around protein amino terminus of D-N-carbamoyl-α-amino acid amidohydrolase derived from Pseudomonas sp. KNK 003A (FERM BP-3181):

A purified amidohydrolase preparation from Pseudomonas sp. KNK 003A (FERM BP-3181) obtained in Example 15 was charged in a reverse-phase HPLC column, and eluted with a concentration gradient of acetonitrile. This fraction containing the amidohydrolase was charged for analysis in a gas-phase protein sequencer, and it was found that the amidohydrolase is a protein having a sequence in the amino terminus portion, which consists of 1st to 20th amino acids of SEQ ID No. 2 in the accompanying Sequence Listing.

Example 17

Purification of D-N-carbamoyl-α-amino acid amidohydrolase produced by transformed *Escherichia coli*:

*Escherichia coli* JM 109.pAD 108 obtained in Example 4 and *Escherichia coli* JM 109.pPD 304 obtained in Example 5 were cultivated by the method as described in Example 6. The bacterial cells were collected from each culture solution by centrifugation, and ultrasonicated. After removal of the residue, these crude enzyme solutions were analyzed by SDS-polyacrylamide electrophoresis. With respect to a suspension of the cultivated and disintegrated bacterial cells of *Escherichia coli JM* 109.pAD 108, the amidohydrolase migrated to the position corresponding to the molecular weight of about 35,000, and an analysis by densitometer after staining revealed that the amidohydrolase amounted to about 50% of the whole soluble proteins of the bacterial cells. Moreover, with respect to a suspension of the cultivated and disintegrated bacterial cells of *Escherichia coli* JM 109.pPD-304, the amidohydrolase migrated to the position corresponding to the molecular weight of about 38,000, and an analysis by densitometer after staining revealed that the amidohydrolase amounted to about 15% of the whole soluble proteins of the bacterial cells.

Example 18

Determination of protein amino terminal sequence of D-N-carbamoyl-α-amino acid amidohydrolase produced by transformed *Escherichia coli*:

A suspension of the cultivated and disintegrated bacterial cells of *Escherichia coli* JM 109.pAD 108 obtained in Example 17 was subjected to heat treatment at 50° C. for 30 minutes, and after removal of the precipitate by centrifugation, ammonium sulfate was added to give 30% saturation, thereby causing precipitation of protein. The precipitated protein was removed by centrifugation and dissolved in deionized water, followed by desaltization using an NAP-10 column (Pharmacia LKB Biotechnology Co., Ltd.) and charging in a gas-phase protein sequencer. From the results obtained, it was found that there were mixed proteins in approximately the same quantities, one having a sequence in the amino terminus portion, which consists of 1st to 16th amino acids of SEQ ID No. 1 in the accompanying Sequence Listing, and the other having a sequence in the amino terminus portion, which contains an additional methionine residue attached to the amino terminus of the former's sequence.

EFFECT OF THE INVENTION

As described hereinabove, the present invention makes it possible to produce D-α-amino acids from D-N-carbamoyl-α-amino acids with high efficiency by employing gene technology.

---

Figure 1:
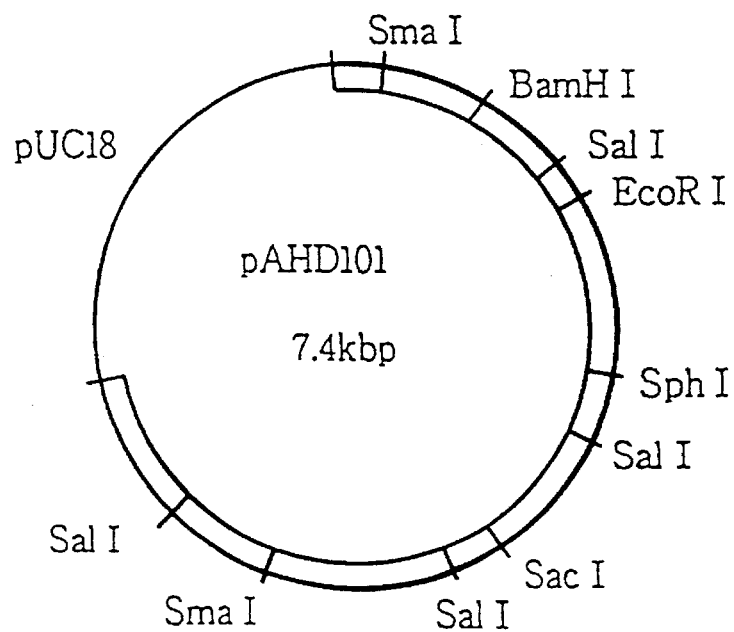
FIG. 1 shows the restriction endonuclease map of plasmid pAHD 101 obtained by the present invention.

We claim:

1. A microorganism including a recombinant DNA comprising vector DNA and a DNA fragment having a gene encoding an enzyme capable of converting D-N-carbamoyl-α-amino acids into the corresponding D-α-amino acids, wherein the gene is isolated from a plasmid selected from the group consisting of pAHD 101, pAD 108, pPHD 301, and pPD 304.

2. A microorganism according to claim 1, wherein said microorganism including the recombinant DNA is a transformant obtained by transforming a host bacterial cell selected from microorganisms belonging to the genus Escherichia, Pseudomonas, Flavobacterium, Bacillus, Serratia, Corynebacterium, or Brevibacterium.

3. A microorganism according to claim 2, wherein said microorganism belonging to the genus Escherichia is *Escherichia coli* JM 109 pAHD 101, *Escherichia coli* JM 109 pAD 108 (FERM BP-3184), *Escherichia coli* JM 109 pPHD 301, or *Escherichia coli* JM 109 pPD 304 (FERM BP-3183).

4. A process for the production of a D-N-carbamoyl-α-amino acid amidohydrolase characterized by using a transformant which is obtained by transformation of host bacterial cells with a recombinant DNA comprising vector DNA and a DNA fragment having a gene encoding a D-N-carbamoyl-α-amino acid amidohydrolase capable of converting D-N-carbamoyl-α-amino acids by removal of their carbamoyl groups into the corresponding D-α-amino-acids, wherein the gene is isolated from a plasmid selected from the group consisting of pAHD 101, pAD 108, pPHD 101, and pPD 304.

5. A process according to claim 4, wherein D-N-carbamoyl-α-amino acid is a compound of the general formula:

R—CH(NHCONH$_2$)—COOH (where R is phenyl, phenyl substituted hydroxy, alkyl, substituted alkyl, aralkyl, or thienyl).

Figure 2:
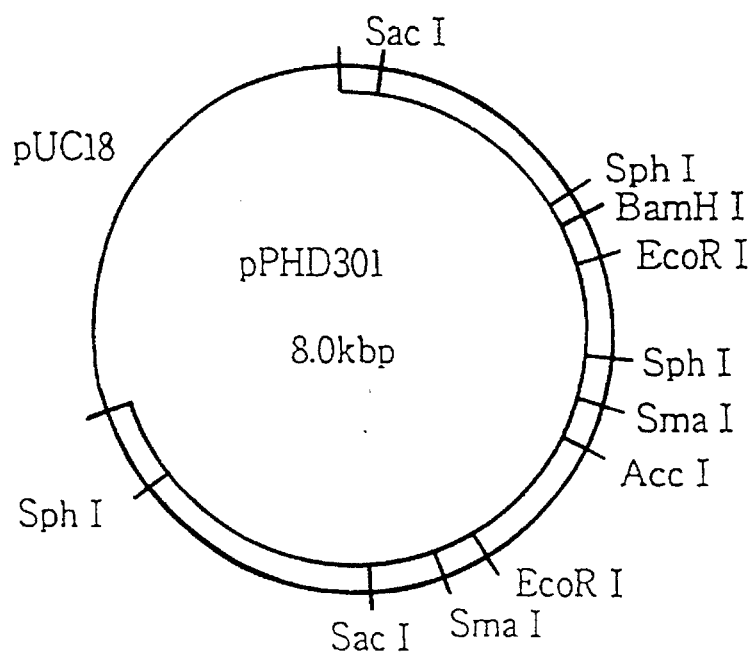
FIG. 2 shows the restriction endonuclease map of plasmid pPHD 301 obtained by the present invention.
Figure 3:
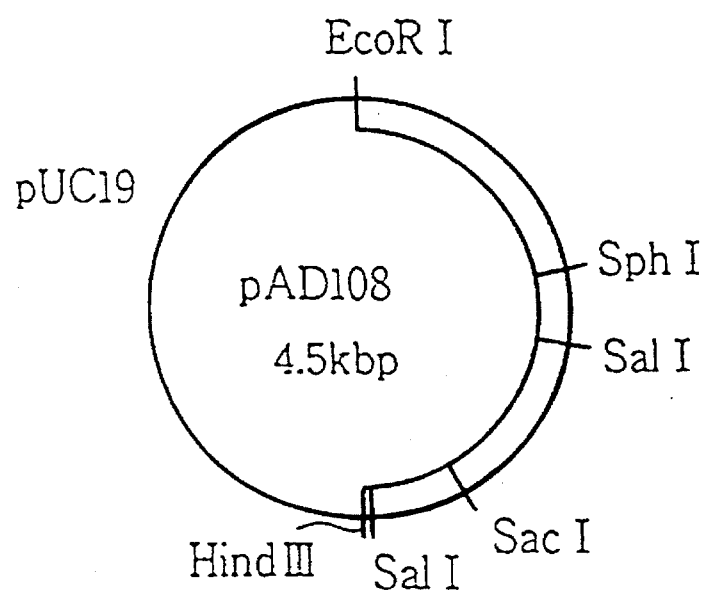
FIG. 3 shows the restriction endonuclease map of plasmid pAD 108 obtained by the present invention.
Figure 4:
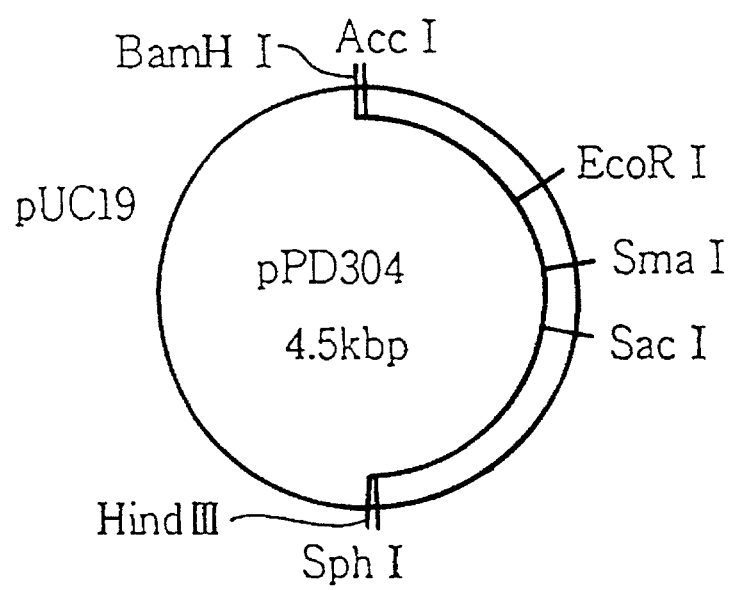
FIG. 4 shows the restriction endonuclease map of plasmid pPD 304 obtained by the present invention.

6. A recombinant plasmid which is obtained by recombination of plasmid pUC 18 or pUC 19 with a DNA fragment having any one of the restriction endonuclease maps of FIGS. 1–4 and containing a gene encoding a D-N-carbamoyl-α-amino acid amidohydrolase derived from Pseudomonas sp. KNK 003A (FERM BP-3181) or *Agrobacterium radiobacter* KNK 712 (FERM BP-1900).

7. A gene for a protein having the enzyme activity to convert D-N-carbamoyl-α-amino acids by removal of their carbamoyl groups into the corresponding D-α-amino acids, said gene encoding the amino acid sequence of 1st to 303rd amino acids shown in SEQ ID No. 1 in the accompanying Sequence Listing.

8. A DNA fragment in which the base sequence of 167th to 232nd bases of SEQ ID No. 1 in the accompanying Sequence Listing is attached to the upstream of the 5' end of the gene according to claim 7.

9. A DNA fragment having the base sequence of 1st to 1785th bases of SEQ ID No. 1 in the accompanying Sequence Listing, and containing a gene of a protein which has the enzyme activity to convert D-N-carbamoyl-α-amino acids by removal of their carbamoyl groups into their corresponding D-α-amino acids.

10. A DNA fragment according to claim 9, which comprises a DNA fragment encoding the amino acid sequence of 1st to 20th amino acids of SEQ ID No. 1 in the accompanying Sequence Listing.

11. A gene encoding a protein having the enzyme activity to convert D-N-carbamoyl-α-amino-acids by removal of their carbamoyl groups into the corresponding D-α-amino acids, said gene encoding the amino acid sequence of 1st to 311th amino acids of SEQ ID No. 2 in the accompanying Sequence Listing.

12. A DNA fragment having the base sequence of 1st to 1820th bases of SEQ ID No. 4 in the accompanying Sequence Listing, or having a base sequence encoding the same amino acid sequence as encoded by the base sequence of SEQ ID No. 4, and containing a gene of a protein which has the enzyme activity to convert D-N-carbamoyl-α-amino acids by removal of their carbamoyl groups into the corresponding D-α-amino acids.

13. A DNA fragment according to claim 12, which comprises a DNA fragment encoding the amino acid sequence of 1st to 20th amino acids of SEQ ID No. 4 in the accompanying Sequence Listing.

* * * * *